United States Patent [19]

Dillon

[11] Patent Number: 5,480,860
[45] Date of Patent: * Jan. 2, 1996

[54] METHODS FOR REDUCING SULFIDES IN SEWAGE GAS

[75] Inventor: Edward T. Dillon, Pasadena, Tex.

[73] Assignee: Petrolite Corporation, St. Louis, Mo.

[ * ] Notice: The portion of the term of this patent subsequent to Dec. 18, 2007, has been disclaimed.

[21] Appl. No.: 371,667

[22] Filed: Jan. 12, 1995

Related U.S. Application Data

[63] Continuation of Ser. No. 200,857, Feb. 22, 1994, abandoned, which is a continuation of Ser. No. 837,554, Feb. 14, 1992, abandoned, which is a continuation of Ser. No. 557,255, Jul. 24, 1990, abandoned, which is a continuation-in-part of Ser. No. 452,539, Dec. 18, 1989, Pat. No. 4,978,512, which is a continuation-in-part of Ser. No. 289,352, Dec. 23, 1988, abandoned.

[51] Int. Cl.$^6$ .......................... B01D 53/48; B01D 53/52
[52] U.S. Cl. .......................... 423/228; 423/226; 423/229
[58] Field of Search .......................... 423/226, 228, 423/229; 424/76.5

[56] References Cited

U.S. PATENT DOCUMENTS

| | | | |
|---|---|---|---|
| 2,496,596 | 2/1950 | Moyer et al. | 252/8.555 |
| 2,596,273 | 5/1952 | Moyer et al. | 252/8.555 |
| 2,596,425 | 5/1952 | Moyer et al. | 252/8.555 |
| 2,761,818 | 9/1956 | Draemel et al. | 196/32 |
| 2,776,870 | 1/1957 | Fischer | 23/2 |
| 2,801,216 | 6/1957 | Yoder et al. | 514/705 |
| 2,860,030 | 11/1958 | Goldtrap et al. | 23/3 |
| 3,981,998 | 9/1976 | Waldstein | 514/241 |
| 4,107,270 | 8/1978 | Ferrin et al. | 423/226 |
| 4,112,049 | 9/1978 | Bozzelli et al. | 423/226 |
| 4,202,882 | 5/1980 | Schwartz | 424/76.5 |
| 4,267,162 | 5/1981 | Maier | 423/542 |
| 4,368,059 | 1/1983 | Doerges et al. | 55/73 |
| 4,405,580 | 9/1983 | Stogryn et al. | 423/228 |
| 4,435,371 | 3/1984 | Frech et al. | 423/231 |
| 4,436,713 | 3/1984 | Olson | 423/573 |
| 4,443,423 | 4/1984 | Olson | 423/573 |
| 4,455,287 | 6/1984 | Primack et al. | 423/226 |
| 4,498,911 | 2/1985 | Deal et al. | 55/32 |
| 4,515,759 | 5/1985 | Burns et al. | 423/220 |
| 4,530,827 | 7/1985 | Heisel et al. | 423/575 |
| 4,532,116 | 7/1985 | Doerges et al. | 423/226 |
| 4,578,208 | 3/1986 | Geke et al. | 252/135 |
| 4,748,011 | 5/1988 | Baize | 423/228 |
| 4,802,996 | 2/1989 | Mouché | 210/764 |
| 4,925,582 | 5/1990 | Bennett | 252/77 |
| 4,978,512 | 12/1990 | Dillon | 423/228 |
| 5,061,373 | 10/1991 | Gallup | 423/226 |
| 5,128,049 | 7/1992 | Gatlin | 423/228 |

FOREIGN PATENT DOCUMENTS

| | | |
|---|---|---|
| 2-180698 | 7/1990 | Japan . |
| 9007467 | 7/1990 | WIPO . |

OTHER PUBLICATIONS

Database WPI, Section Ch., Week 9034, *Derwent Publications Ltd.*, London, GB; Class D15, AN 90–257479 & JP–A–2 180 698 (DIAFLOC KK) 13 Jul. 1990, Abstract.
Database WPI, Section Ch, *Dersent Publications Ltd.*, London, GB; Class A97, AN 73–76406U & JP–A–48 063 987 (agency Ind Science Techno), Abstract (1975).
J. F. Walker, "Formaldehyde", Reinhold, New York, 1964, pp. 360–361.
EPA Design Manual "Odor and Corrosion Control in Sanitary Sewerage Systems and Treatment Plants", EPA/625/1–85/018 (1985).
"Odor and Corrosion Control in Sanitary Sewerage Systems and Treatment Plants", Bowker et al., Noyes Data Corporation, pp. 52–61 and 70–79.
Walker, J. F., *Formaldehyde*, Reinhold Publishing Co., New York, p. 247 (1975).
Reexamination Certificate–B1–4,978,512 for U.S. Patent. Certificate issued Jun. 15, 1993.

*Primary Examiner*—Wayne Langel
*Assistant Examiner*—Peter T. DiMauro
*Attorney, Agent, or Firm*—Panitch Schwarze Jacobs & Nadel

[57] ABSTRACT

Methods are provided for selectively reducing the levels of hydrogen sulfide and organic sulfides in sewage gas to reduce or remove the odor, toxicity and corrosivity associated therewith, comprising contacting said sewage gas with a composition comprising a trisubstituted hexahydro-s-triazine.

25 Claims, No Drawings

METHODS FOR REDUCING SULFIDES IN SEWAGE GAS

CROSS-REFERENCE TO RELATED APPLICATIONS

This application is a continuation of U.S. patent application Ser. No. 08/200,857, filed Feb. 22, 1994, which is in turn a continuation of Ser. No. 07/837,544, filed Feb. 14, 1992, which in turn is a continuation of Ser. No. 07/557,255, filed Jul. 24, 1990, all now abandoned, the latter being a continuation-in-part of our U.S. patent application Ser. No. 452,539, filed Dec. 18, 1989, now U.S. Pat. No. 4,978,512, which is a continuation-in-part of our U.S. patent application Ser. No. 289,352, filed Dec. 23, 1988, now abandoned, for "Composition and Method of Sweetening Natural Gas".

FIELD OF THE INVENTION

The present invention relates to methods for controlling odor, toxicity and corrosion of sulfides in sewage gas. More specifically, this invention relates to methods for reducing the hydrogen sulfide and organic sulfide levels in sewage gas systems.

BACKGROUND OF THE INVENTION

Sewage gas contains hydrogen sulfide and other organic sulfides which cause it to be malodorous. Also, the majority of the chemical compounds which cause the odor in sewage gas also cause it to be toxic and corrosive. Numerous sulfur-containing substances have been identified as causing the odor in sewage gas. Examples of these compounds are allyl mercaptan, amyl mercaptan, benzyl mercaptan, crotyl mercaptan, dimethyl sulfide, ethyl mercaptan, hydrogen sulfide, methyl mercaptan, propyl mercaptan, sulfur dioxide, tert-butyl mercaptan, thiocresol and thiophenol, to name a few.

However, hydrogen sulfide is generally one of the main components of sewage gas, being usually contained in relatively high concentrations therein. Accordingly, the degree to which hydrogen sulfide is present in a sample of sewage gas is used as a measure of the odor intensity and corrosiveness of that particular sample.

Not only will hydrogen sulfide cause an intense odor in sewage gas, this compound can have numerous physiological effects and can be quite hazardous. For example, the odor associated with hydrogen sulfide ("rotten eggs") can be detected when the concentration of the hydrogen sulfide is as low as about 0.1 parts per million of sewage gas. As the concentration of the hydrogen sulfide increases, various physical effects are seen, such as headache, nausea, throat and eye irritation, etc. Once the hydrogen sulfide level reaches a concentration of about 500 parts per million of sewage gas or more, serious life threatening effects will result, such as pulmonary edema, nervous system stimulation and apnea. If the hydrogen sulfide level were to reach a concentration of between about 1,000 to 2,000 parts per million of sewage gas, respiratory collapse and paralysis resulting in death may result.

Traditional sanitary sewer design practice has not fully acknowledged the importance of eliminating corrosion and controlling the odor caused by sulfides. This is evidenced by the widespread occurrence of these problems in conventional sewage treatment systems. In conventional systems, odor problems are managed by ventilating sewer systems so that the sewage gas becomes diluted with air. Although this practice may reduce gas concentrations to less than toxic levels and may be useful for controlling corrosion, large volumes of malodorous gas are produced.

In order to address this odor problem, such air-diluted sewage gas is often further chemically treated. For example, offending odors can be made less objectionable through the use of odor-masking and counter-active agents such as vanillin and juniper oil. An example of this method is disclosed in, e.g., *EPA Design Manual*, "Odor and Corrosion Control in Sanitary Sewage Systems and Treatment Plants", EPA/625/1-85/018, pp 71–93 (1985). However, this approach merely involves replacing an objectionable odor with a more pleasant one. Accordingly, this method is generally the least preferred of the available techniques for reducing sewage gas odor.

Also, strong oxidizing agents, such as chlorine, hydrogen peroxide and strong alkalis, such as sodium hydroxide and lime, have been used to react with the offending substances present in sewage gas. An example of these methods is set forth in "Odor and Corrosion Control in Sanitary Sewage Systems and Treatment Plants", Bowker et al, Noyes Data Corporation, pp 52–60 and 71–78 (1989). However, these approaches have generally not proven to be commercially and/or economically successful since, although removal rates may appear high, the concentration of malodorous components in the treated sewage gas remains above threshold levels for odor detection.

Since such sulfide-containing sewage gas or sludge gas (i.e., gas resulting from waste water or waste water constituents which have undergone anaerobic decomposition) is present in nearly all conventional sewage treatment systems, it can be seen that there is a need for an effective and efficient method for reducing the levels of hydrogen sulfide and other organic sulfides in waste water treatment systems. Such a method is needed, not only to remove the offensive odor and corrosivity associated with the sewage gas, but to reduce the possible occurrence of the adverse physiological effects discussed above.

SUMMARY OF THE INVENTION

The above-stated objectives are obtained by the present method for selectively reducing the levels of hydrogen sulfide and organic sulfides from sewage gas to remove the odor and corrosivity associated therewith, which comprises contacting the sewage gas with a composition comprising a trisubstituted hexahydro-s-triazine. This method may be used in various installations, such as a lift station fume exhauster or wet scrubber system,

DETAILED DESCRIPTION OF THE PREFERRED EMBODIMENTS

Preferred sulfide-reducing agents for use in the present invention are compounds of the following Formula I:

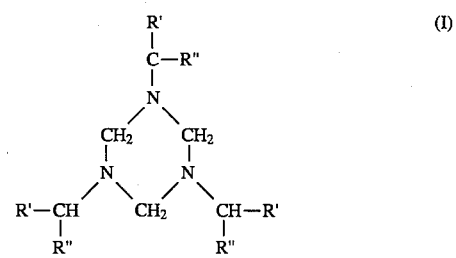

wherein R' is hydrogen; lower alkyl, such as $CH_3$—, $CH_3CH_2$—, $CH_3CH_2CH_2$—, $(CH_3)_2CH$—; hydroxyalkyls of lower alkyl groups, such as $HOCH_2CH_2$—, $HOCH_2$—, $HO(CH_3)CH$—; and N,N-dialkylalkylene amines of lower alkyl groups, such as $(CH_3)_2NCH_2$— or $(C_2H_5)_2NCH_2$—; and R" is selected from hydrogen or lower alkyl, such as $CH_3$—, or $CH_3CH_2$—. As used herein "lower" generally means $C_1$ to $C_6$, and preferably $C_1$ to $C_3$.

In particularly preferred embodiments, R' is $HOCH_2$—, $HOCH_2CH_2$— or $HO(CH_3)CH$— and R" is H or $CH_3$. In the presently most preferred embodiment, the compound of Formula I is N,N',N"-tris(2-hydroxyethyl)hexahydro-s-triazine.

The compounds of Formula I employed in the method of the present invention may be prepared by reacting formaldehyde and a primary amine. Preferred primary amines for use in preparing the compounds of Formula I are:

(II)

wherein R' and R" are defined as set forth above for Formula I. The formaldehyde and the primary amine may be reacted in any ratio which will produce the desired triazines in the desired amounts. Appropriate ratios for specific instances will be evident to one skilled in the art, based upon the present disclosure. However, preferably, the formaldehyde and primary amine are reacted in a ratio of 1:1.

The reaction may be carried out by any appropriate means known in the art. However, in the presently preferred embodiment, gaseous or aqueous formaldehyde may be reacted directly with the primary amine. Alternatively, solid paraformaldehyde may be used instead of the gaseous or aqueous formaldehyde and be reacted directly with the primary amine. The preferred procedure comprises mixing the primary amine with gaseous formaldehyde or an aqueous solution of formaldehyde at a temperature of about 35° to about 60° C. for about 30 to about 45 minutes. Once the reaction is complete, the water formed during the course of the reaction may be removed from the resultant reaction mixture by appropriate means. For example, the water may be removed by azeotropic distillation, distillation in vacuo, etc. The reaction mixture containing the trisubstituted hexahydro-s-triazines of the present invention is then ready for use in the present method. However, if desired, the resulting reaction mixture may be used directly in the method of the present invention without removing the water formed during the reaction.

Commercially available trisubstituted hexahydro-s-triazines, such as Grotan® by Ciba-Geigy of Summit, N.J., which is a preparation of N,N',N"-tris(2-hydroxyethyl)hexahydro-s-triazine, may be used in the present method. Such commercially available triazines are generally marketed for use as biocides, but may find use in the present method.

The composition contacted with the sewage gas in accordance with the present method may comprise one or more of the above triazines in an amount of about 20 to about 80 weight percent and preferably about 25 to about 40 weight percent by total weight of the composition.

The compositions useful in the present method may further comprise water and a lower mono- or dihydric alcohol as a medium for the triazines. Preferably, the alcohol is a lower alcohol of about 1 to about 3 carbons. More preferably, the mono- or dihydric alcohols are selected from the group consisting of $CH_3OH$, $CH_3CH_2OH$, $(CH_3)_2CHOH$ and $HOCH_2CH_2OH$.

The compositions may contain water in an amount of about 20 to about 80 weight percent and preferably about 48 to about 60 weight percent of the total composition. The compositions may also comprise about 0 to about 60 weight percent and preferably about 12 to about 20 weight percent of the mono- or dihydric alcohol per total weight of the composition.

The present method provides a selective and nearly instantaneous reaction with the malodorous and corrosive sulfides present in sewage gas, producing no precipitates, solids or deleterious environmental effects. Moreover, the efficacy of the reduction of hydrogen sulfide and other organic sulfide compounds is not affected by the concentration of carbon dioxide in the sewage gas, the temperature of the gas or the pressure of the system. However, it has been determined that good results are achieved when the following conditions exist: the carbon dioxide concentration in the gas to be treated is about 0.03 to about 5.0% by volume; the temperature of the gas is maintained in the range of about 0° to about 93° C.; and the pressure of the system is maintained in the range of about 5 to about 500 psig. However, the present method is not limited to the above-noted reaction conditions.

The above triazines selectively react with sulfides present in sewage gas streams regardless of the $CO_2$ level in the sewage gas, forming water soluble products. The water soluble products formed appear to be predominantly water soluble dithiazines and non-volatile organic sulfides as determined by $^{13}C$ NMR analysis and comparison to model systems.

Once formed, the water soluble products may be removed from the sewage treatment system by any appropriate means, and the system may then be recharged with an appropriate amount of fresh or unreacted triazine composition. That is, once the composition containing the triazine compound has reached its saturation point (i.e., once all of the triazine has reacted with the sulfides present in the sewage gas), the saturated composition may be removed and the sewage treatment system recharged with an appropriate amount of a "fresh" composition comprising the triazine compound. It can be determined that the saturation point has been reached by monitoring the gas exiting the scrubber for the presence of sulfides.

The triazines useful in the invention are extremely selective in their ability to react with sulfides, e.g., hydrogen sulfides, carbonyl sulfides, carbon disulfides, etc., in the presence of any amount of carbon dioxide. Such selective removal of sulfides is advantageous and economical, particularly in systems wherein a simultaneous reduction in the amount of carbon dioxide is not required or desirable. Also, this selective removal is much more efficient than conventional systems in which the carbon dioxide competes with the sulfides for reaction with the active compound.

In the selective removal of hydrogen sulfide and other organic sulfides from sewage gas, the present invention may be used in combination with any known, conventional sewage gas treatment method, including absorptive processes (such as those using activated carbon), as well as chemical injection treatments (such as those injecting sodium hydroxide or sodium hydroxide/sodium hypochlorite mixtures into the sewage system).

The present method may be carried out by directly injecting the reaction product into the sewage gas flow lines, as well as directly into the sewage itself. Alternatively, the sewage gas may be bubbled through a layer of the present composition or the present composition may be introduced into the system by atomizers in the ducting or inlet systems feeding wet scrubbers. Moreover, the present method may be carried out by contacting the gas with the triazine compositions in wet scrubbers placed at appropriate points in the system. When using the wet scrubbers, preferably, the compositions of the invention are allowed to contact the sewage gas by counter-current flow or cross-flow and most preferably, conventional packing and/or baffling systems are used to increase the contact between the compositions of the invention and the sewage gas. In any method of introduction into the sewage system, the present composition should be contacted with the sewage gas for a period of time sufficient to reduce the sulfide levels to the desired concentration. Appropriate lengths of time will be evident to the artisan based upon the present disclosure.

The present method may be used at any point in a waste water treatment system which will provide efficient and economical results. Preferably, the compositions containing the present reaction product are contacted with the sewage gas at the points of the sewage treatment system commonly known as the lift station fume exhauster or digester, as these are generally the most odorous points of the system.

Generally, about 6.5 to about 9.5 g of a 25% aqueous solution of the triazine compound will effectively remove 1.0 g of hydrogen sulfide from sewage gas. This corresponds to about 0.03 to about 0.10 gallons of a 25% solution of the compound per 1 ppm $H_2S$ per MMscf.

Generally, in any system in which the present method is employed, the reaction temperature of the composition with the hydrogen sulfide and/or other organic sulfides in the sewage gas should be maintained at about 32° to about 200° F. and preferably 60° to about 180° F.

The sulfide level in a sewage gas system may be reduced to about 0 ppm when the method of the present invention is employed. The determination of the sulfide level in the sewage gas systems may be made by various methods known to those skilled in the art. For example, the sulfide level may be determined by passing the gas exiting the system into colorimetric tubes, such as "Dräger Tubes" which comprise lead acetate on a solid support. A change in color in the lead acetate indicates the presence of a specific concentration of organic sulfide. Alternatively, electrochemical sensors, metal oxide semiconductors and/or IR spectroscopy may be used to determine the parts per million concentration of sulfide in the sewage gas. Each of these methods are applied at the point of the sewage gas treatment system when the gas exits the system.

The invention will now be illustrated further with reference to the following specific, non-limiting examples.

PREPARATION EXAMPLES

Example 1

N,N',N"-tris(2-N,N-dimethylaminoethyl) hexahydro-s-triazine

One mole of N,N-dimethylethylenediamine was stirred at 30° C. in a reaction flask, while one mole of aqueous formaldehyde was added dropwise thereto over a 40 minute period. During the addition of the aqueous formaldehyde, the temperature of the reaction mixture was maintained at 50°–55° C. After the addition of the aqueous formaldehyde was complete, stirring was continued for 30 minutes. The reaction water was distilled off and the resulting product was isolated, purified and identified as the compound indicated above.

Example 2

N,N',N"-tris(2-hydroxyethyl)hexahydro-s-triazine

One mole of 37% aqueous formaldehyde was added to one mole of monoethanolamine at 60° C. with stirring. Following the addition of the formaldehyde, stirring was continued for additional 30 minutes and the mixture was cooled to room temperature. The water of reaction was then removed by vacuum distillation and the N,N',N"-tris(2-hydroxyethyl)hexahydro-s-triazine was isolated by fractional distillation in vacuo.

USE EXAMPLES

Example 3

A 25% solution of N,N',N"-tris(2-hydroxyethyl)hexahydro-s-triazine in a medium of 58.8% water and 16.2% methanol was tested in a typical scrubber system in a waste water treatment plant. The plant typically utilized activated carbon/caustic in a 4 ft. diameter by 7 ft. height scrubber. The system was charged with a 25% solution of the indicated triazine compound. Polypropylene packing was added to the scrubber to yield improved contact between the composition and the malodorous gases. Prior to treatment, the gas was generally found to contain about 35 parts per million (ppm) of hydrogen sulfide. After treatment was initiated with the indicated solution, the hydrogen sulfide level was reduced to 0 ppm in the gas exiting the scrubber. The hydrogen sulfide level remained at 0 ppm throughout 65 days of treatment. During this period, 220 gallons of the triazine solution were charged into the scrubber.

Example 4

80 gallons of a 25% solution of N,N',N"-tris(2-hydroxyethyl)hexahydro-s-triazine in 58.8% water and 16.2% methanol was used in a scrubbing unit in a lift station. Prior to charging the system with the 25% triazine solution, the hydrogen sulfide level of the gas effluent was found to be about 18 ppm. Five minutes after charging the scrubber with the triazine solution, the hydrogen sulfide level of the gas exiting the scrubber was 0 ppm. The hydrogen sulfide level was maintained at 0 ppm for the 72 days in which the scrubber was charged with the 25% triazine solution.

Example 5

220 gallons of a 50% solution of N,N',N"-tris(2-hydroxyethyl)hexahydro-s-triazine in 58.8% water and 16.2% methanol was tested in a 8 ft. diameter by 16 ft. height scrubber in a waste water plant lift station. Previously, this facility employed a conventional sodium hypochlorite solution treatment which generally yielded a hydrogen sulfide level of about 55 ppm in the gas exiting the scrubber. After the addition of the 50% triazine solution, a rapid drop of the hydrogen sulfide level in the exiting gas to 0 ppm was observed. The level of hydrogen sulfide remained constant at 0 ppm during 28 days of treatment.

Example 6

220 gallons of a 50% solution of N,N',N"-tris(2-hydroxyethyl)hexahydro-s-triazine in 58.8% water and 16.2% methanol was charged to a 6 ft. diameter by 16 ft. height scrubber in a waste water treatment plant mixing tank and thickener. The previous chemical treatment at this plant comprised the addition of a 50% sodium hydroxide solution to the system, typically resulting in hydrogen sulfide levels of about 40 ppm. After addition of the 50% triazine solution, the hydrogen sulfide levels in the gas exiting the scrubber were observed to be 0 ppm. The hydrogen sulfide level remained constant at 0 ppm for 24 days.

Example 7

The following laboratory example was designed to simulate actual use conditions in order to demonstrate the superior effectiveness of the present method.

An experimental apparatus was devised which comprised the following components connected in tandem:

- a lecture bottle;
- a flow meter;
- a flask;
- a flow meter;
- an infrared spectrometer;
- an air trap;
- a sodium hydroxide trap;
- a dry ice and acetone trap;
- an air trap; and
- a water trap.

The performance capabilities of the present method to complex and retain the various sulfide compounds present in waste water and municipal waste plant effluents was determined as follows.

Sulfide gases were introduced at a flow rate of 46–60 ml min$^{-1}$ into the apparatus containing 10% solutions of the triazine solutions identified in Tables 1 and 2 as A, B and C, with subsequent monitoring of the process by IR spectroscopy. The sulfide gases were also treated with water and a conventional 10% NaOH solution for purposes of comparison. The results of the testing are set forth below in Tables 1 and 2.

TABLE 1

|  | A | B | C | NaOH | Water |
|---|---|---|---|---|---|
| Grams of H$_2$S complexed per gram of treating compound | 0.61 | 0.6 | 0.43 | .84 | — |
| Moles of H$_2$S complexed per mole of treating compound | 4.0 | 2.2 | 4.0 | 1.0 | — |
| Grams of H$_2$S complexed per 100 g of a 10% aqueous solution of treating compound, using gas comprised of 100% H$_2$S | 6.3 | 6.2 | 4.5 | 8.6 | .3 |
| Grams of H$_2$S complexed per 100 g of a 10% aqueous solution of treating compound, using a gas comprised of 50% H$_2$S and 50% CO$_2$ | 6.3 | 6.2 | — | 4.0 | — |
| Grams of H$_2$S complexed per 100 g of a 10% aqueous solution of treating compound, using a gas comprised of 5% H$_2$S and 95% CO$_2$ | 6.1 | 6.2 | — | .7 | — |

A = N,N',N''-tris(2-hydroxyethyl) hexahydro-s-triazine
B = 1,3,5-trimethylhexahydro-s-triazine
C = N,N',N'',-tris(2-dimethylaminoethyl) hexahydro-s-triazine

TABLE 2

|  | A | B | Water |
|---|---|---|---|
| Grams of CH$_3$SH complexed per gram of triazine | 0.6 | 0.6 | — |
| Moles of CH$_3$SH complexed per mole of triazine | 3.0 | 2.0 | — |
| Grams of CH$_3$SH complexed per 100 g of 10% aqueous solution of triazine | 7.79 | 7.49 | 1.49 |

A = N,N',N''-tris(2-hydroxyethyl) hexahydro-s-triazine (R' = HOCH$_2$-, R'' = H')
B = 1,3,5-trimethylhexahydro-s-triazine (R' = R'' = H)

Table 1 demonstrates the effectiveness of the compounds of Formula I in complexing malodorous hydrogen sulfide, while Table 2 demonstrates the effectiveness of the compounds of Formula I in complexing malodorous methanethiol. As can be seen from Tables 1 and 2, the triazines of present Formula I are much more effective than the conventional NaOH solution in removing both hydrogen sulfide and methanethiol in the presence of carbon dioxide. This effect increases dramatically as the percentage of carbon dioxide in the sulfide gas increases.

The present invention may be embodied in other specific forms without departing from the spirit or essential attributes thereof and, accordingly, reference should be made to the appended claims, rather than to the foregoing specification, as indicating the scope of the invention.

I claim:

1. A method for reducing the levels of sulfides present in gaseous discharge from a waste water treatment system, comprising contacting fluids in said waste water system with a triazine composition comprising a reaction product of (i) a compound of formula NH$_2$—CHR'—R'', where R' is H, an alkyl group of 1 to 6 carbons, a hydroxyalkyl of an alkyl group of 1 to 6 carbons or an N,N-dialkylalkylene amine of an alkyl group of 1 to 6 carbons and R'' is H or an alkyl group of 1 to 6 carbons and (ii) formaldehyde or paraformaldehyde, said reaction product consisting essentially of a hexahydrotriazine, said triazine contacting step substantially reducing the level of sulfides in said gaseous discharge, said sulfide reduction being due predominantly to the conversion of said sulfides to dithiazines.

2. A method according to claim 1, wherein the fluid contacted is the gaseous discharge from the waste water system.

3. A method according to claim 1, wherein the fluid contacted is the waste water.

4. A method as in claim 1, wherein said hexahydrotriazine is represented by

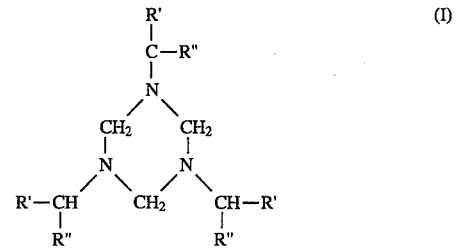

wherein R' is H, an alkyl group of 1 to 6 carbons, a hydroxyalkyl of an alkyl group of 1 to 6 carbons or an N-N-dialkylalkylene amine of an alkyl group of 1 to 6 carbons and R'' is H or an alkyl group of 1 to 6 carbons.

5. A method as in claim 4, wherein R' is H, $CH_3$—, $CH_3CH_2$—, $CH_3CH_2CH_2$—, $(CH_3)_2CH$—, $HOCH_2CH_2$—, $HOCH_2$—, $HO(CH_3)CH$—, $(CH_3)_2NCH_2$— or $(C_2H_5)_2NCH_2$—; and R" is H, $CH_3$— or $CH_3CH_2$—.

6. A method as in claim 1, wherein said composition further contains water and a mono- or dihydric alcohol of 1 to 6 carbons.

7. A method as in claim 6, wherein said alcohol is selected from the group consisting of $CH_3OH$, $CH_3CH_2OH$, $(CH_3)_2CHOH$ and $HOCH_2CH_2OH$.

8. A method as in claim 4, wherein R' is $HOCH_2$—, $HOCH_2CH_2$—or $HO(CH_3)CH$— and R" is H or $CH_3$—.

9. A method as in claim 1, wherein said hexahydrotriazine is N,N',N"-tris(2-hydroxyethyl)hexahydro-s-triazine.

10. A method as in claim 6, wherein said composition comprises 20 to 80 weight percent of a compound of Formula I, 20 to 80 weight percent of water and 0 to 60 weight percent of a mono- or dihydric alcohol of 1 to 6 carbons.

11. A method as in claim 6, wherein said composition comprises 25 to 40 weight percent of a compound of Formula I, 48 to 60 weight percent of water and 12 to 20 weight percent of a mono- or dihydric alcohol of 1 to 6 carbons.

12. A method as in claim 1, wherein said sulfides are selected from the group consisting of hydrogen sulfide, organic sulfides, carbonyl sulfides, and carbon disulfide.

13. A method as in claim 1, wherein said hexahydrotriazine is a trisubstituted hexahydro-s-triazine.

14. A method as in claim 1, wherein the sulfide-containing stream includes carbon dioxide.

15. A method comprising the step of contacting a gas stream comprising a sulfide selected from the group consisting of hydrogen sulfide and methyl mercaptan, with a triazine composition comprising a reaction product of (i) a compound of formula $NH_2$—$CHR'$—R", where R' is H, an alkyl group of 1 to 6 carbons, a hydroxyalkyl of an alkyl group of 1 to 6 carbons or an N,N-dialkylalkylene amine of an alkyl group of 1 to 6 carbons and R" is H or an alkyl of 1 to 6 carbons and (ii) formaldehyde or paraformaldehyde, said reaction product consisting essentially of a hexahydrotriazine, said method comprising reduction of sulfide in the gas due predominantly to the conversion of sulfide to dithiazines.

16. A method as in claim 15, wherein said hexahydrotriazine is represented by

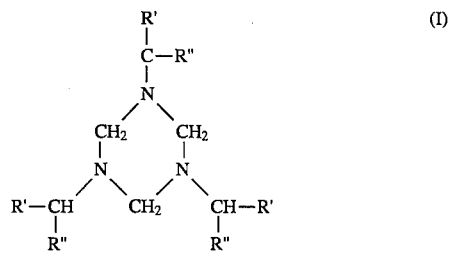

wherein R' is H, an alkyl group of 1 to 6 carbons, a hydroxyalkyl of an alkyl group of 1 to 6 carbons or an N-N-dialkylalkylene amine of an alkyl group of 1 to 6 carbons; and R" is H or an alkyl group of 1 to 6 carbons.

17. A method as in claim 16, wherein R' is H, $CH_3$—, $CH_3CH_2$—, $CH_3CH_2CH_2$—, $(CH_3)_2CH$—, $HOCH_2CH_2$—, $HOCH_2$—, $HO(CH_3)CH$—, $(CH_3)_2NCH_2$— or $(C_2H_5)_2NCH_2$—; and R" is H, $CH_3$— or $CH_3CH_2$—.

18. A method as in claim 16, wherein R' is $HOCH_2$—, $HOCH_2CH_2$— or $HO(CH_3)CH$— and R" is H or $CH_3$.

19. A method as in claim 15, wherein said composition further contains water and a mono- or dihydric alcohol of 1 to about 6 carbons.

20. A method as in claim 19, wherein said composition comprises 20 to 80 weight percent of a compound of Formula I, 20 to 80 weight percent of water and 0 to 60 weight percent of a mono- or dihydric alcohol of 1 to 6 carbons.

21. A method as in claim 19, wherein said composition comprises 25 to 40 weight percent of a compound of Formula I, 48 to 60 weight percent of water and 12 to 20 weight percent of a mono- or dihydric alcohol of 1 to 6 carbons.

22. A method as in claim 18, wherein said alcohol is selected from the group consisting of $CH_2OH$, $CH_3CH_2OH$, $(CH_3)_2CHOH$ and $HOCH_2CH_2OH$.

23. A method as in claim 15, wherein said hexahydrotriazine is N,N',N"-tris(2-hydroxyethyl)hexahydro-s-triazine.

24. A method as in claim 15, wherein said hexahydrotriazine is a trisubstituted hexahydro-s-triazine.

25. A method as in claim 15, wherein the gas stream includes carbon dioxide.

* * * * *